United States Patent
Hamawaki et al.

(10) Patent No.: US 7,993,635 B2
(45) Date of Patent: Aug. 9, 2011

(54) MENTHOL-CONTAINING FORMULATION

(75) Inventors: Tomonori Hamawaki, Izumisano (JP); Yosuke Kataoka, Izumisano (JP); Takako Isoda, Izumisano (JP)

(73) Assignee: Nihon Pharamaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/458,876

(22) Filed: Jul. 27, 2009

(65) Prior Publication Data

US 2009/0292028 A1 Nov. 26, 2009

Related U.S. Application Data

(63) Continuation of application No. 10/559,731, filed as application No. PCT/JP2004/009096 on Jun. 28, 2004, now abandoned.

(30) Foreign Application Priority Data

Jun. 30, 2003 (JP) .................................. 2003-186493

(51) Int. Cl.
*A61K 9/107* (2006.01)
(52) U.S. Cl. ................ 424/78.05; 424/747; 514/13.2; 604/516
(58) Field of Classification Search ............... 424/78.05, 424/747; 514/13.2; 604/516
See application file for complete search history.

(56) References Cited

U.S. PATENT DOCUMENTS

| | | | | |
|---|---|---|---|---|
| 3,422,189 | A * | 1/1969 | Rider | 424/724 |
| 6,897,195 | B2 | 5/2005 | Su et al. | |
| 2002/0068092 | A1 * | 6/2002 | Bosch et al. | 424/501 |
| 2003/0147927 | A1 * | 8/2003 | Khan et al. | 424/400 |

FOREIGN PATENT DOCUMENTS

| | | |
|---|---|---|
| GB | 2006011 | * 10/1978 |
| JP | 6-56623 | 3/1994 |
| JP | 2003-292450 | 10/2003 |
| WO | 92/06947 | 4/1992 |
| WO | 03/097026 | 11/2003 |
| WO | 03/097027 | 11/2003 |

OTHER PUBLICATIONS

International Search Report issued Oct. 26, 2004 in connection with International Application No. PCT/JP2004/009096.
Asao, T. et al., "An easy method for the intraluminal administration of peppermint oil before colonoscopy and its effectiveness in reducing colonic spasm", Gatrointestinal Endoscopy, vol. 53, No. 2, pp. 172-177 (2001).
Morita, M. et al. "Quantitative Structure-Spasmolytic Activity Relationships of Terpenoids and Their Derivatives from *Alpinia speciosa, Alpinia japonica* and *Atractylodes lancea*", Natural Med., vol. 52, No. 1, pp. 22-31 (1998).
Hiki, N. et al. "Shokakan Naishikyo Kensa ni Okeru Peppermint oil Kan Konai", Dai 10 Kai Clinical Video Forum (CVF), p. 73 (2002).

* cited by examiner

*Primary Examiner* — Fereydoun G Sajjadi
*Assistant Examiner* — Danielle Sullivan
(74) *Attorney, Agent, or Firm* — Wenderoth, Lind & Ponack, L.L.P.

(57) ABSTRACT

It is known that L-menthol controls smooth muscle contraction. In order to use L-menthol in practice as a digestive tract contraction inhibiting agent in digestive tract endoscopy, it is required to devise means of giving a formulation in which an L-menthol-containing formulation remains stable and transparent or little cloudy over a long time after the production and which shows little foaming at the administration. In the present invention, an antifoaming agent is further added to a formulation for inhibiting smooth muscle contraction or a peristaltic contraction in a digestive tract containing a L-menthol emulsion having an average particle size of less than 100 nm.

Thus, it is possible to obtain a formulation that remains stable over a long time, has a high light transmittance, and produces little foam when filled into a container and sprayed at a target area to inhibit contraction to facilitate observation of the area in endoscopic examination of the digestive tract etc.

16 Claims, 1 Drawing Sheet

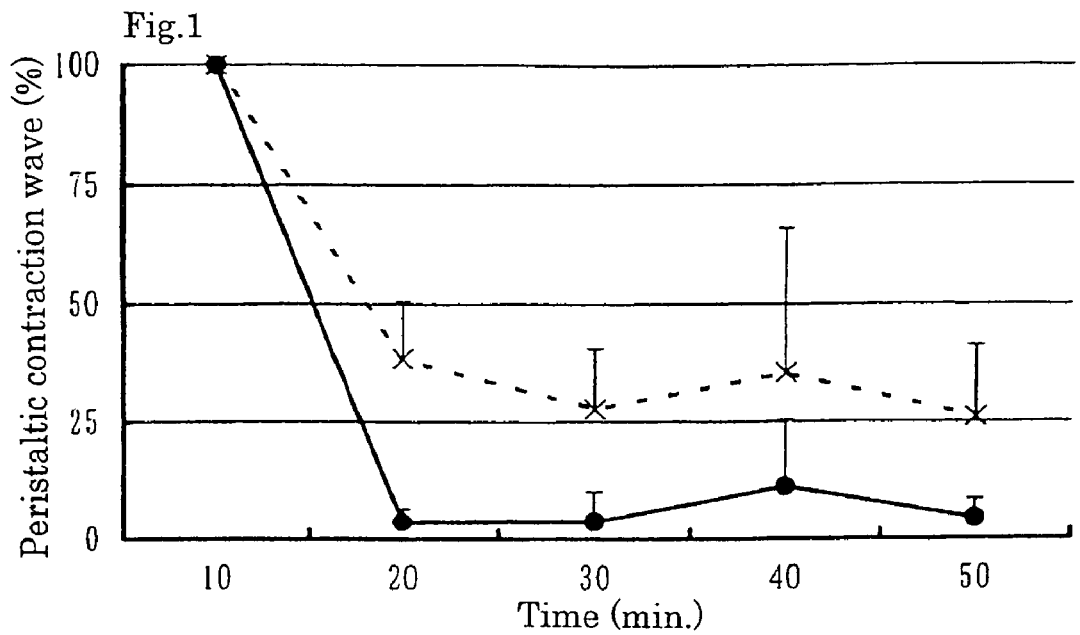
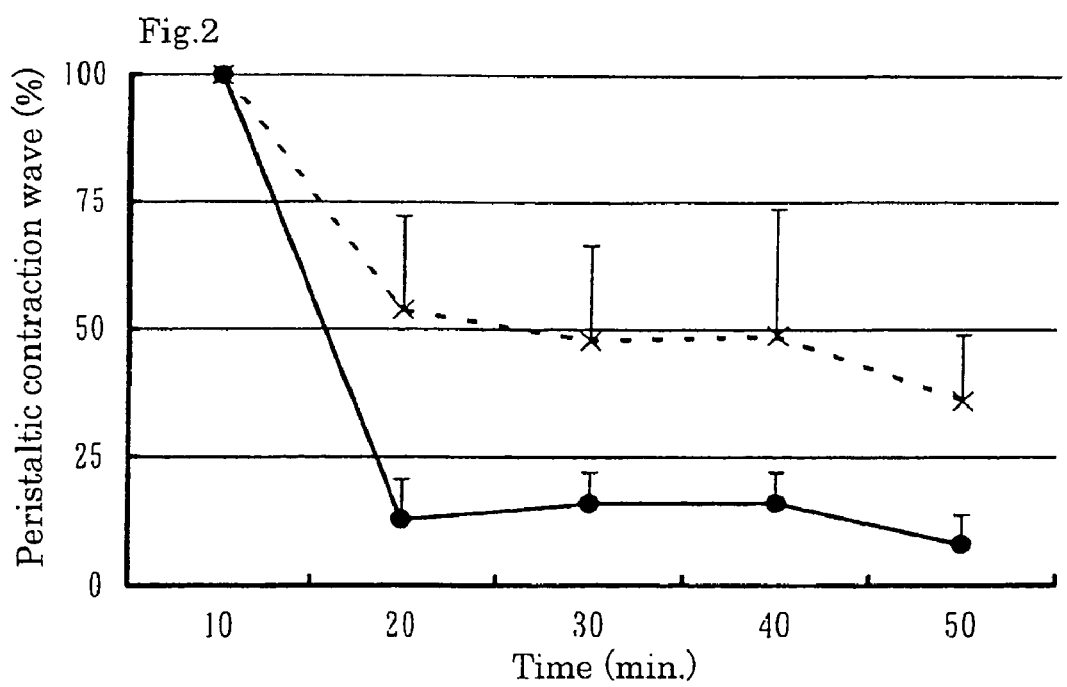

MENTHOL-CONTAINING FORMULATION

This application is a continuation of application Ser. No. 10/559,731, filed Dec. 7, 2005 now abandoned which is the National Stage of International Application No. PCT/JP2004/009096, filed Jun. 28, 2004.

TECHNICAL FIELD

The present invention relates to an L-menthol-containing formulation for inhibiting smooth muscle contraction or peristalsis, particularly a formulation for inhibiting digestive tract contraction, which remains stable over a long time, exhibits high light transmittance, and produces little foam when sprayed at a target area to inhibit contraction to facilitate observation of the area in endoscopic examination of the digestive tract etc.

BACKGROUND ART

Excessive contraction of the digestive tract during endoscopic examination of the digestive tract such as stomach and large intestine prevents correct diagnosis and allows a minute lesion such as a small-sized carcinoma to be missed.

As a contraction inhibitor for endoscopic examination of the digestive tract, an anti-cholinergic agent scopolamine butylbromide (Trade name: Buscopan Injection, Nippon Boehringer Ingelheim Co., Ltd.) or glucagon has conventionally been prescribed. However scopolamine butylbromide is contraindicated in a patient with glaucoma, prostatic hypertrophy, or arrhythmia, and glucagon has some problems including its very weak effect in inhibition of digestive tract contraction. Scopolamine butylbromide has to be injected immediately before or during the examination because it is to be injected intravenously or intramuscularly.

In addition some of the formulations may cause disorder of accommodation or vertigo after administration, so that the person who received administration of such a formulation for the examination should refrain for example from driving a car for a while after completion of the examination.

Accordingly, in an attempt to solve the problems mentioned above, an investigation was made recently to produce a digestive tract contraction inhibitor formulation using peppermint oil (Gastrointestinal Endoscopy, Vol. 53, No. 2, 172-177 (2001).

For production of formulations of such an inhibitor, the conventional methods disclosed include a method in which peppermint oil and water are mixed by stirring and allowed to stand at room temperature for 24 hours and only the transparent portion after elimination of the oily component floating on the surface of the water is used, and a method in which after mixing by stirring and standing at room temperature for 24 hours, an aqueous layer is filtered to remove an oily component before use. The formulations produced by these methods, however, have a risk of loss of the volatile peppermint oil by evaporation while standing at room temperature for a long time, and thus have a problem that the content of peppermint oil at the time of administration to a patient may be inconstant or indefinite. Consequently a constant amount of a conventionally-formulated product may fail to produce a constant effect when administered for example by spraying as a gastric contraction inhibitor onto the wall of stomach, which results in an insufficient inhibitory effect on contraction. Furthermore, these products require formulation just before use because of their difficulty in long-term storage and the quality of the formulation may be variable from site to site of medical practice.

DISCLOSURE OF INVENTION

Problem to be Solved by the Invention

The present inventors succeeded in development of a smooth muscle contraction inhibitor formulation or a digestive tract contraction inhibitor formulation containing L-menthol which remains stable for a long time and transparent by emulsifying L-menthol and a fat or oil with a surfactant, and filed an application for patent. This inhibitor formulation, however, required a relatively high content of the surfactant for transparency so that foaming occurred during filling the formulation into a container or during spraying through a tube to the affected area for endoscopic examination, and the foam made observation of the affected area difficult. Under these circumstances, development of an L-menthol-containing digestive tract contraction inhibitor formulation that has good transparency, namely high light transmittance, and is less foamy and remains stable for a long time has ardently been desired.

Means for Solving the Problem

As a result of the inventor's extensive research to obtain an L-menthol-containing formulation for inhibiting smooth muscle contraction, especially for inhibiting digestive tract contraction that remains stable for a long time, exhibits highly light transmittance, and hardly causes foaming during filling into a container or administration to a target region, the inventors have found that an L-menthol-containing formulation that hardly causes foaming during filling or use of the formulation, is good in transmittance, and remains stable for a long time can be obtained by addition of a small amount of an antifoaming agent to a mixture of L-menthol, a surfactant and water, and making the average particle size of the emulsion particles less than 100 nm, and finally have accomplished the present invention.

Namely the invention relates to:

(1) An L-menthol-containing formulation for inhibiting smooth muscle contraction, which comprises L-menthol, a surfactant, and an antifoaming agent and which is an emulsion with an average particle size of less than 100 nm;

(2) The L-menthol-containing formulation according to (1), which further comprises a fat or oil;

(3) The L-menthol-containing formulation according to (1) or (2), which has a light transmittance of 50% or more;

(4) The L-menthol-containing formulation according to any one of (1) to (3), which comprises 0.01 to 5.0% by weight of L-menthol, 0.1 to 10% by weight of a surfactant, and 0.0001 to 0.01% by weight of an antifoaming agent based on the weight of the whole formulation;

(5) The L-menthol-containing formulation according to (4), wherein a content of the fat or oil is from 0.1 to 10% by weight;

(6) The L-menthol-containing formulation according to any one of (1) to (5), wherein the antifoaming agent is at least one agent selected from silicone antifoaming agents; and (7) The L-menthol-containing formulation according to any one of (1) to (6), wherein the surfactant is at least one member selected from polyoxyethylene hydrogenated caster oils and sucrose fatty acid esters.

The L-menthol employed in the invention is not particularly limited as to its origin, being generally a main component of peppermint oil. Peppermint oil is obtained by steam distillation of a plant for example of *Mentha piperita* or *Mentha arvensis* and contains 30% or more by weight of L-menthol. The L-menthol-containing material employed may be peppermint oil or *mentha* oil as it is, but highly purified L-menthol obtained for example by fractional distillation of peppermint oil or *mentha* oil can also be employed preferably. More preferably L-menthol of a purity of 90% or more by weight is employed. Recently L-menthol is produced also by synthesis. In any way the one in compliance with the Japanese Pharmacopoeia standard of L-menthol is preferable.

In the present invention, L-menthol is present in an amount of 0.01 to 5.0% by weight, preferably 0.1 to 3.0% by weight, and more preferably 0.3 to 1.5% by weight based on the entire weight of the formulation.

The antifoaming agent employed in the invention is not limited particularly as long as it is an antifoaming agent that can be employed in a pharmaceutical product, and a mixture of two or more antifoaming agents may be used. Silicone antifoaming agents are preferable, agents of the polydimethylsiloxane series are particularly preferable, and polydimethylsiloxane-silicone dioxide mixture is more preferable.

The amount of the antifoaming agent employed in the invention is usually 0.0001 to 0.01% by weight, preferably 0.0005 to 0.007% by weight, and more preferably 0.0007 to 0.005% by weight based on the entire formulation.

The surfactant employed in the invention is not limited particularly as long as it is a surfactant that can be employed in a pharmaceutical product, and a mixture of two or more surfactants may be used. The amount of the surfactant is usually 0.1 to 10% by weight, preferably 0.5 to 5% by weight based on the entire formulation. The surfactant of the invention preferably contains at least polyoxyethylene hydrogenated caster oil. The amount of polyoxyethylene hydrogenated caster oil, when contained, is usually 1 to 3% by weight, preferably 1.5 to 2.5% by weight based on the entire formulation. Sucrose fatty acid ester and polysorbate may be used preferably, and polysorbate 80 etc. can be used particularly preferably.

In addition to polyoxyethylene hydrogenated caster oil, other surfactants that can be employed in pharmaceutical products, such as edible nonionic surfactants and ionic surfactants, may be employed alone or in combination thereof.

A formulation of the present invention can be obtained by stirring water that contains the above-mentioned L-menthol, surfactant, and antifoaming agent, and, if necessary, also the fat or oil, with heating, or by heating the mixture after mixing by stirring.

Antifoaming effect of the emulsion thus obtained as a smooth muscle contraction inhibitor formulation of the invention was evaluated based on the time for disappearance of foam after 1-minute shaking of 20 mL of a sample in a 30-mL glass bottle of 33 mm in diameter in a shaker (170 shakes/min, stroke: 40 mm). The time for disappearance of foam of the formulation of the invention is preferably not more than 3 minutes, more preferably not more than 30 seconds, and particularly preferably not more than 20 seconds.

The average particle size of the emulsion as a smooth muscle contraction inhibitor formulation of the invention is less than 100 nm, preferably not more than 70 nm, more preferably not more than 50 nm, and particularly preferably not more than 30 nm.

The average particle size of the emulsion was determined by placing a few drops of the sample in a 10-mm cell and adding distilled water to obtain a sample solution, followed by measurement using a light scattering photometer (ELS8000, OTSUKA ELECTRONICS CO., LTD).

An emulsion having a large average particle size gives a white turbid formulation, and when such a formulation is sprayed onto the affected area for endoscopic examination of the digestive tract etc., observation of the area may be difficult. In contrast, the emulsion obtained in the invention is a clear or slightly turbid liquid with foaming suppressed and thus is free of problems mentioned above.

The light transmittance of the formulation of the invention is preferably 50% or more and particularly preferably 70% or more.

The light transmittance was measured by placing a sample in a 10-mm cell using a double beam spectrophotometer Model U-2001 (HITACHI, LTD.) at 900 nm as a measurement wavelength.

The formulation of the invention can be obtained by means of a known emulsification or solubilization. A preferred method is one of those listed below, to which it is not limited.

i) First, L-menthol is dissolved in a fat or oil. The dissolution may be conducted at room temperature or with warming. Then the resultant uniform mixture of the L-menthol and the fat or oil is added to water containing a surfactant which has been dispersed well by stirring for example with a stirrer such as homomixer, and the mixture is stirred thoroughly using a stirrer such as a homomixer. If necessary, a further ultrasonic treatment or use of a high-pressure emulsifier may be employed additionally to ensure uniform and fine particles of the emulsion. Thereafter, the emulsion thus prepared is autoclaved at 115° C. for 30 minutes.

ii) In another method, a formulation is prepared by the method described above, and stored at 60° C. or a higher temperature for about 1 week instead of the autoclave sterilization.

iii) In still another method, a surfactant is added to water and dispersed using a stirrer such as a homomixer, and thereafter L-menthol and a fat or oil are added, and the mixture is stirred at about 80° C. for about 10 minutes with a homomixer.

For the formulation for inhibiting smooth muscle contraction of the present invention, a fat or oil can be used. The fat or oil to be used is not particularly limited as far as it is a pharmaceutically acceptable fat or oil, but preferably a middle-chain fatty acid triglyceride (MCT) or a long-chain fatty acid triglyceride (LCT) such as soybean oil, olive oil, and coconut oil can be used.

MCT that can be used includes those with C6- to C12-fatty acid moiety, and a mixture of those with different carbon numbers can be used (for example, 'Panasate 800' manufactured by NOF Corporation, 'Coconad RK' manufactured by KAO Corporation).

The fat or oil can be used as a solvent for L-menthol, where 0.5- to 10-fold weight, preferably 1- to 5-fold weight, of the fat or oil can be used per weight of L-menthol. The fat or oil is used in an amount usually of 0.1 to 5% by weight, preferably 0.5 to 3% by weight, based on the weight of the entire emulsion.

The contraction inhibitory formulation containing a fat or oil may be prepared by stirring L-menthol, a fat or oil, a surfactant, and water containing an antifoaming agent, and heating while stirring, or heating after stirring can produce a more stable formulation.

Heat treatment can be accomplished by a method which is not limited specifically, and it is acceptable to heat an L-menthol-containing emulsion, which contains L-menthol, a fat or oil, a surfactant, and an antifoaming agent, at any stage during the course of manufacturing. Examples of the heat treatment may be a procedure in which emulsification of the mixture is performed for example with a homomixer under a heating condition, in which emulsification of the mixture is performed using a high pressure emulsifier under a heating condition, in which the emulsion is filled in a container which is then sterilized by heating, in which the emulsion is filled in a container which is then stored at a high temperature, or in which the emulsification is performed under a heating condition followed by sterilization also under a heating condition. Heating time may vary depending on the stirring condition, and it is desirable to maintain the heating condition for 1 minute to 14 days, preferably for 5 minutes to 6 hours.

The heating temperature may be 60° C. or higher, preferably 70° C. to 130° C., especially preferably 80° C. to 121° C. A satisfactory result is obtained when heating sterilization is performed under the heating condition usually employed for an ordinary fat emulsion (110 to 121° C.).

Another active ingredient, a thickening agent, a stabilizer, a preservative, etc. may be added appropriately as needed.

The thickening agent may be carrageenan, methyl cellulose, carboxymethyl cellulose, guar gum, pectin, or the like. Addition of the thickening agent can adjust the falling-down rate of the formulation sprayed inside the digestive tract to a desirable rate.

The amount of the thickening agent to be added may vary according to the type of the thickening agent and is usually selected from the range from 0.01 to 5% by weight.

The stabilizer may be sodium edetate and the preservative may be sorbic acid, benzalkonium chloride, a parabene, or the like, in a suitable amount.

The L-menthol-containing formulation of the invention is sprayed directly onto the target area, for example the inner side of the digestive tract, via a sprayer or an endoscopic forceps guide, in laparotomic or endoscopic surgery of the digestive tract, in endoscopic examination of the digestive tract, or in any medical care that requires inhibition of the digestive tract contraction. For direct administration of a constant amount of emulsion via a sprayer or an endoscopic forceps guide, it is desirable to fill the unit dose of the emulsion that has been prepared as described above into an extrusive vessel such as a pre-filled syringe. It is a matter of course that the product of the invention can be filled and stored in a container such as a vial or ampoule.

The formulation of the invention remains stable even after storage for a long term. For example, the average particle size of the emulsion does not exceed 100 nm and the light transmittance does not become below 50% after storage at 25° C. for 1 month.

Effect of the Invention

The formulation for inhibiting smooth muscle contraction, the emulsion of the invention remains stable over a long time, exhibits a high light transmittance, and causes little foam during filling in a container or in use, namely in administration. Therefore the formulation is useful as a contraction inhibitor to be used particularly in endoscopic examination of the digestive tract.

BRIEF DESCRIPTION OF THE DRAWINGS

FIG. 1 shows the percent change of peristaltic contraction wave area of the body of stomach of dog in Experimental Example 2.

FIG. 2 shows the percent change of peristaltic contraction wave area of the pyloric part of stomach of dog in Experimental Example 2.

DESCRIPTION OF REFERENCE NUMERALS

The solid line with the marks ● indicates a graph for the composition in Example 7, and the dotted line with the marks X indicates a graph of the untreated case.

BEST MODE FOR CARRYING OUT THE INVENTION

The invention is described in more detail in the following Examples, Comparative Examples, and Experimental Examples.

Example 1

To 200 mL of water were added 4.0 g of polysorbate 80 (Tween 80, Rheodol TW-O120V, KAO Corporation) and 0.02 g of a polydimethylsiloxane-silicone dioxide mixture (KS-69, Shin-Etsu Chemical Co., Ltd.), followed by emulsification with a homomixer (liquid temperature: 60° C.) to give a polydimethylsiloxane-silicone dioxide mixture fluid. To 1600 mL of water were added 20.0 g of a sucrose fatty acid ester (Surfhope J1616, Mitsubishi-Kagaku Foods Corporation), 36.0 g of polyoxyethylene hydrogenated caster oil 60, (NIKKOL HCO-60, Nikko Chemicals Co., Ltd.), and 30.0 g of MCT (Coconad RK, Kao Corporation) were added and dispersed with a homomixer. To this liquid were added 16.0 g of L-menthol that was in compliance with the Japanese Pharmacopoeia standard (L-Menthol, The SUZUKI Menthol CO., LTD.) and the polydimethylsiloxane-silicone dioxide mixture fluid, followed by emulsification with a homomixer at a liquid temperature of 80° C. Water was added to this liquid to make the entire volume 2000 mL to give a desired emulsion. The average particle size of this emulsion was 28.5 nm with the light transmittance of 96.09%.

Example 2

To 200 mL of water were added 4.0 g of Tween 80 (Rheodol TW-O120V, KAO Corporation) and 0.06 g of a polydimethylsiloxane-silicone dioxide mixture (KS-69, Shin-Etsu Chemical Co., Ltd.), followed by emulsification with a homomixer (liquid temperature: 60° C.) to give a polydimethylsiloxane-silicone dioxide mixture fluid. To 1600 mL of water were added 20.0 g of a sucrose fatty acid ester (Surfhope J1616, Mitsubishi-Kagaku Foods Corporation), 36.0 g of HCO-60 (NIKKOL HCO-60, Nikko Chemicals Co., Ltd.), and 30.0 g of MCT (Coconad RK, Kao Corporation) and dispersed with a homomixer. To this liquid were added 16.0 g of L-menthol that was in compliance with the Japanese Pharmacopoeia standard (L-Menthol, The SUZUKI Menthol CO., LTD.) and the polydimethylsiloxane-silicone dioxide mixture fluid, followed by emulsification with a homomixer at a liquid temperature of 80° C. Water was added to this liquid to make the entire volume 2000 mL to give a desired emulsion. The average particle size of this emulsion was 28.8 nm with the light transmittance of 94.68%.

Example 3

To 200 mL of water were added 4.0 g of Tween 80 (Rheodol TW-O120V, KAO Corporation) and 0.10 g of a polydimethylsiloxane-silicone dioxide mixture (KS-69, Shin-Etsu Chemical Co., Ltd.), followed by emulsification with a homomixer (liquid temperature: 60° C.) to give a polydimethylsiloxane-silicone dioxide mixture fluid. To 1600 mL of water were added 20.0 g of a sucrose fatty acid ester (Surfhope J1616, Mitsubishi-Kagaku Foods Corporation), 36.0 g of HCO-60 (NIKKOL HCO-60, Nikko Chemicals Co., Ltd.), and 30.0 g of MCT (Coconad RK, Kao Corporation) and dispersed with a homomixer. To this liquid were added 16.0 g of L-menthol that was in compliance with the Japanese Pharmacopoeia standard (L-Menthol, The SUZUKI Menthol CO., LTD.) and the polydimethylsiloxane-silicone dioxide mixture fluid, followed by emulsification with a homomixer at a liquid temperature of 80° C. Water was added to this liquid to make the entire volume 2000 mL to give a desired emulsion. The average particle size of this emulsion was 27.7 nm with the light transmittance of 93.72%.

Example 4

To 200 mL of water were added 4.0 g of Tween 80 (Rheodol TW-O120V, KAO Corporation) and 0.02 g of a polydimethylsiloxane-silicone dioxide mixture (KS-66, Shin-Etsu Chemical Co., Ltd.), followed by emulsification with a homomixer (liquid temperature: 60° C.) to give a polydimethylsiloxane-silicone dioxide mixture fluid. To 1600 mL of water were added 20.0 g of a sucrose fatty acid ester (Surfhope J1616, Mitsubishi-Kagaku Foods Corporation), 36.0 g of HCO-60 (NIKKOL HCO-60, Nikko Chemicals Co., Ltd.), and 30.0 g of MCT (Coconad RK, Kao Corporation) and dispersed with a homomixer. To this liquid were added 16.0 g of L-menthol that was in compliance with the Japanese Pharmacopoeia standard (L-Menthol, The SUZUKI Menthol CO., LTD.) and the polydimethylsiloxane-silicone dioxide mixture fluid, followed by emulsification with a homomixer at a liquid temperature of 80° C. Water was added to this liquid to make the entire volume 2000 mL to give a desired emulsion. The average particle size of this emulsion was 27.6 nm with the light transmittance of 95.75%.

Example 5

To 200 mL of water were added 4.0 g of Tween 80 (Rheodol TW-O120V, KAO Corporation) and 0.06 g of a polydimethylsiloxane-silicone dioxide mixture (KS-66, Shin-Etsu Chemical Co., Ltd.), followed by emulsification with a homomixer (liquid temperature: 60° C.) to give a polydimethylsiloxane-silicone dioxide mixture fluid. To 1600 mL of water were added 20.0 g of a sucrose fatty acid ester (Surfhope J1616, Mitsubishi-Kagaku Foods Corporation), 36.0 g of HCO-60 (NIKKOL HCO-60, Nikko Chemicals Co., Ltd.), and 30.0 g of MCT (Coconad RK, Kao Corporation) and dispersed with a homomixer. To this liquid were added 16.0 g of L-menthol that was in compliance with the Japanese Pharmacopoeia standard (L-Menthol, The SUZUKI Menthol CO., LTD.) and the polydimethylsiloxane-silicone dioxide mixture fluid, followed by emulsification with a homomixer at a liquid temperature of 80° C. Water was added to this liquid to make the entire volume 2000 mL to give a desired emulsion. The average particle size of this emulsion was 26.3 nm with the light transmittance of 94.16%.

Example 6

A mixture of 4.0 g of Tween 80 (Rheodol TW-O120V, KAO Corporation) and 0.10 g of a polydimethylsiloxane-silicone dioxide (KS-66, Shin-Etsu Chemical Co., Ltd.) were added to 200 mL of water, followed by emulsification with a homomixer (liquid temperature: 60° C.) to give a polydimethylsiloxane-silicone dioxide mixture fluid. To 1600 mL of water were added 20.0 g of a sucrose fatty acid ester (Surfhope J1616, Mitsubishi-Kagaku Foods Corporation), 36.0 g of HCO-60 (NIKKOL HCO-60, Nikko Chemicals Co., Ltd.), and 30.0 g of MCT (Coconad RK, Kao Corporation) and dispersed with a homomixer. To this liquid were added 16.0 g of L-menthol that was in compliance with the Japanese Pharmacopoeia standard (L-Menthol, The SUZUKI Menthol CO., LTD.) and the polydimethylsiloxane-silicone dioxide mixture fluid, followed by emulsification with a homomixer at a liquid temperature of 80° C. Water was added to this liquid to make the entire volume 2000 mL to give the desired emulsion. The average particle size of this emulsion was 27.2 nm with the light transmittance of 92.58%.

Example 7

To 200 mL of water were added 4.0 g of Tween 80 (Rheodol TW-O120V, KAO Corporation) and 0.02 g of a polydimethylsiloxane-silicone dioxide mixture (KS-66, Shin-Etsu Chemical Co., Ltd.), followed by emulsification with a homomixer (liquid temperature: 60° C.) to give a polydimethylsiloxane-silicone dioxide mixture fluid. To 1600 mL of water were added 20.0 g of a sucrose fatty acid ester (Surfhope J1616, Mitsubishi-Kagaku Foods Corporation), 36.0 g of HCO-60 (NIKKOL HCO-60, Nikko Chemicals Co., Ltd.), and 24.0 g of MCT (Coconad RK, Kao Corporation) and dispersed with a homomixer. To this liquid were added 16.0 g of L-menthol that was in compliance with the Japanese Pharmacopoeia standard (L-Menthol, The SUZUKI Menthol CO., LTD.) and the polydimethylsiloxane-silicone dioxide mixture fluid, followed by emulsification with a homomixer at the liquid temperature of 80° C. Water was added to this liquid to make the entire volume 2000 mL to give a desired emulsion. The average particle size of this emulsion was 23.2 μm with the light transmittance of 97.34%.

Comparative Example 1

1.12 g of L-menthol that was in compliance with the Japanese Pharmacopoeia standard (L-menthol, The SUZUKI Menthol CO., LTD.) and 2.8 g of MCT (Coconad RK, Kao Corporation) were mixed and dissolved in a water bath at 60° C. to give an L-menthol solution. Water, 60 mL was added to 0.28 g of Tween 80 (Rheodol TW-O120V, KAO Corporation), 1.68 g of a sucrose fatty acid ester (Surfhope J1616, Mitsubishi-Kagaku Foods Corporation), and 2.8 g of HCO-60 (NIKKOL HCO-60, Nikko Chemicals Co., Ltd.), followed by dispersion with a homomixer (60° C. in a water bath). To this liquid was added the L-menthol solution, followed by emulsification with a homomixer (60° C. in a water bath). Then water was added to this liquid to make the entire volume 140 mL, followed by ultrasonic emulsification for 10 minutes to give an emulsion. Then the emulsion was autoclaved at 115° C. for 20 minutes to give a desired emulsion. The average particle size of this emulsion was 30.3 nm with the light transmittance of 97.48%.

Experimental Example 1

Into a 30-mL bottle, 20 mL of a sample was placed and the bottle was shaken for 1 minute in a shaker SR-IIW (Taiyo Kagaku Kogyo Co., Ltd., 170 shakes/min, 40 nm stroke).

After 1-minute shaking, the time for disappearance of foam was measured. The results of the measurement are shown together with average particle sizes and light transmittance in Table 1.

TABLE 1

| Example or Comparative Example | Average particle size at initial (nm) | Light transmittance at initial (%) | Average particle size after storage for 1 month at 25° C. (nm) | Light transmittance after storage for 1 month at 25° C. (%) | Time for disappearing of foams |
| --- | --- | --- | --- | --- | --- |
| Example 1 | 28.5 | 96.09 | 33.7 | 93.80 | 4 sec. |
| Example 2 | 28.8 | 94.68 | 34.4 | 92.46 | 4 sec. |
| Example 3 | 27.7 | 93.72 | 37.6 | 90.11 | 4 sec. |
| Example 4 | 27.6 | 95.75 | 31.0 | 94.11 | 3 sec. |
| Example 5 | 26.3 | 94.16 | 30.7 | 91.82 | 3 sec. |
| Example 6 | 27.2 | 92.58 | 32.5 | 98.62 | 3 sec. |
| Example 7 | 23.2 | 97.34 | 25.9 | 96.16 | 6 sec. |
| Comparative Example 1 | 30.3 | 97.48 | — | — | 6.5 hr |

As evident from Table 1, all of the formulations obtained in Examples of the invention had an average particle size as about 1.2-fold large as the initial particle size not only immediately after formulation but also even after storage at 25° C. for 1 month, with a light transmittance of 95% or more of the initial value, and foam disappeared in a very short time, the time for disappearance being 6 seconds or less. In contrast the average particle size and the initial light transmittance of the emulsion obtained in Comparative Example 1 were not very different from those of the emulsions obtained in Examples, but 6 hours and 30 minutes was required for disappearance of foam.

Experimental Example 2

Inhibitory Effect on Stomach Contraction of Anesthetized Dog

Materials and Methods

To a dog (about 10 kg) which had been kept fasting over day and night, atropine sulfate as a pre-anesthetic medication was intravenously injected followed by intravenous injection of thiopental sodium for induction of anesthesia. An intratracheal tube was inserted and fixed. A mixture gas of nitrous oxide and oxygen was blown into. Isoflurane was sent via the isoflurane vaporizer. The concentration of isoflurane was elevated gradually from 0.5% for maintenance anesthesia. The anesthetized dog was laparotomized at the median line, and a strain gauge force transducer (SGT) was fixed in the body of stomach and at the pyloric part of stomach according to the conventional procedure.

Ten minutes after completion of IMC (inter-digestive migrating contraction), erythromycin at 6 mg/animal was intravenously administered to induce peristaltic movement of the stomach. Ten more minutes later, 10 ml of the formulation of Example 7 which had been stored at 25° C. for 1 month was administered via a stomach catheter into the body of stomach or to the pyloric part of stomach, and contraction was recorded. Contraction-inhibiting effect was evaluated from the percent change of the wave area at every 10 minutes after administration of the formulation. The results are shown in FIG. 1 and FIG. 2. As a control, the percent change of the wave area without treatment was also determined.

As shown in FIG. 1 and FIG. 2, the contraction inhibitor formulation of the invention, when sprayed on the body or the pyloric part of the stomach after induction of contraction by administration of erythromycin, inhibited significantly more strongly as compared with the untreated stomach. No foam appeared in endoscopy after spraying of the contraction inhibitor formulation, with no disturbance for observation of the area.

INDUSTRIAL APPLICABILITY

The L-menthol-containing formulation for inhibiting smooth muscle contraction of the invention remains stable for a long time after preparation, exhibits a high light transmittance, and hardly causes foaming when administered into the digestive tract, and thus can be used favorably for endoscopic examination of the digestive tract such as esophagus, stomach, small intestine, large intestine, and rectum.

The invention claimed is:

1. A method for inhibiting smooth muscle contraction in a human digestive tract by administering to a human digestive tract an L-menthol-containing formulation which comprises 0.01 to 5.0% by weight of L-menthol, 0.1 to 10% by weight of a surfactant, 0.1 to 10% by weight of a fat or oil and 0.0001 to 0.01% by weight of an antifoaming agent based on the weight of the whole formulation and which is an emulsion with an average particle size of less than 100 nm and has a light transmittance of 50% or more.

2. The method for inhibiting smooth muscle contraction in the digestive tract according to claim 1, wherein the amount of L-menthol is 0.1 to 3.0% by weight based on the weight of the whole formulation.

3. The method for inhibiting smooth muscle contraction in the digestive tract according to claim 1, wherein the surfactant comprises a polyoxyethylene hydrogenated castor oil, sucrose fatty acid ester or polysorbate.

4. The method for inhibiting smooth muscle contraction in the digestive tract according to claim 1, wherein the surfactant comprises a polyoxyethylene hydrogenated castor oil and an edible nonionic surfactant employable in a pharmaceutical product.

5. The method for inhibiting smooth muscle contraction in the digestive tract according to claim 1, wherein the surfactant comprises a polyoxyethylene hydrogenated castor oil, sucrose fatty acid ester and polysorbate.

6. The method for inhibiting smooth muscle contraction in the digestive tract according to claim 1, wherein the amount of the fat or oil is 0.1 to 5% by weight based on the weight of the whole formulation.

7. The method for inhibiting smooth muscle contraction in the digestive tract according to claim 1, wherein the fat or oil is at least one member selected from the group consisting of a middle-chain fatty acid triglyceride and a long-chain fatty acid triglyceride.

8. The method for inhibiting smooth muscle contraction in the digestive tract according to claim 1, wherein the fat or oil is a middle-chain fatty acid triglyceride.

9. The method for inhibiting smooth muscle contraction in the digestive tract according to claim 1, wherein the antifoaming agent is a silicone antifoaming agent.

10. The method for inhibiting smooth muscle contraction in the digestive tract according to claim 1, wherein the amount of the antifoaming agent is 0.0005 to 0.007% by weight based on the whole formulation.

11. The method for inhibiting smooth muscle contraction in the digestive tract according to claim 1, wherein the average particle size of the emulsion is less than 70 nm.

12. The method for inhibiting smooth muscle contraction in the digestive tract according to claim 1, wherein the average particle size of the emulsion is less than 50 nm.

13. The method for inhibiting smooth muscle contraction in the digestive tract according to claim 1, wherein the L-menthol-containing formulation has a light transmittance of 70% or more.

14. The method for inhibiting smooth muscle contraction in the digestive tract according to claim 1, wherein the L-menthol-containing formulation comprises 0.01 to 5.0% by weight of L-menthol, 0.1 to 10% by weight of a surfactant comprising a polyoxyethylene hydrogenated castor oil, sucrose fatty acid ester or polysorbate, 0.1 to 10% by weight of a middle-chain fatty acid triglyceride and 0.0001 to 0.01% by weight of a silicone antifoaming agent based on the whole formulation and which is an emulsion with an average particle size of less than 100 nm and has a light transmittance of 50% or more.

15. The method for inhibiting smooth muscle contraction in the digestive tract according to claim 1, wherein the L-menthol-containing formulation is sprayed directly onto a target area of the digestive tract.

16. The method for inhibiting smooth muscle contraction in the digestive tract according to claim 1, wherein the L-menthol-containing formulation is directly administrated via an endoscopic forceps guide onto a target area of the digestive tract.

* * * * *